US009960253B2

(12) United States Patent
Fife

(10) Patent No.: US 9,960,253 B2
(45) Date of Patent: May 1, 2018

(54) CHEMICALLY SENSITIVE SENSOR WITH LIGHTLY DOPED DRAINS

(71) Applicant: LIFE TECHNOLOGIES CORPORATION, Carlsbad, CA (US)

(72) Inventor: Keith G. Fife, Palo Alto, CA (US)

(73) Assignee: Life Technologies Corporation, Carlsbad, CA (US)

(*) Notice: Subject to any disclaimer, the term of this patent is extended or adjusted under 35 U.S.C. 154(b) by 0 days. days.

(21) Appl. No.: 14/179,453

(22) Filed: Feb. 12, 2014

(65) Prior Publication Data
US 2014/0193938 A1 Jul. 10, 2014

Related U.S. Application Data

(62) Division of application No. 13/173,793, filed on Jun. 30, 2011, now Pat. No. 8,653,567.

(60) Provisional application No. 61/361,403, filed on Jul. 3, 2010.

(51) Int. Cl.
H01L 21/00 (2006.01)
H01L 29/66 (2006.01)
G01N 27/414 (2006.01)
H01L 29/788 (2006.01)
H01L 27/11517 (2017.01)

(52) U.S. Cl.
CPC ....... H01L 29/6659 (2013.01); G01N 27/414 (2013.01); H01L 27/11517 (2013.01); H01L 29/788 (2013.01); G01N 27/4145 (2013.01)

(58) Field of Classification Search
CPC ............. G01N 27/414; G01N 27/4145; H01L 29/6659; H01L 27/11517; H01L 29/788
See application file for complete search history.

(56) References Cited

U.S. PATENT DOCUMENTS

| 4,086,642 A | 4/1978 | Yoshida et al. |
| 4,411,741 A | 10/1983 | Janata |
| 4,437,969 A | 3/1984 | Covington et al. |
| 4,438,354 A | 3/1984 | Haque et al. |
| 4,444,644 A | 4/1984 | Hiramoto |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |

(Continued)

FOREIGN PATENT DOCUMENTS

| CN | 1582334 | 2/2005 |
| CN | 1585896 | 2/2005 |

(Continued)

OTHER PUBLICATIONS

Bockelmann, U. et al., "Detecting DNA by field effect transistor arrays", Proceedings of the 2006 IFIP International Conference on Very Large Scale Integration, 2006, 164-168.

(Continued)

Primary Examiner — Fei Fei Yeung Lopez

(57) ABSTRACT

A chemically sensitive sensor with a lightly doped region that affects an overlap capacitance between a gate and an electrode of the chemical sensitive sensor. The lightly doped region extends beneath and adjacent to a gate region of the chemical sensitive sensor. Modifying the gain of the chemically sensitive sensor is achieved by manipulating the lightly doped region under the electrodes.

5 Claims, 5 Drawing Sheets

(56) References Cited

U.S. PATENT DOCUMENTS

| | | |
|---|---|---|
| 4,701,253 A | 10/1987 | Litenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau |
| 5,110,441 A | 5/1992 | Kinlen et al. |
| 5,113,870 A | 5/1992 | Rossenfeld |
| 5,126,759 A | 6/1992 | Small et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,646,558 A | 7/1997 | Jamshidi et al. |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A | 8/1999 | Rosenblatt |
| 5,958,703 A | 9/1999 | Dower et al. |
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,262,568 B1 | 7/2001 | Komatsu et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,618,083 B1 | 9/2003 | Chen et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,657,269 B2 | 12/2003 | Migliorato et al. |
| 6,671,341 B1 | 12/2003 | Kinget et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,780,591 B2 | 8/2004 | Williams et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakob et al. |
| 7,087,387 B2 | 8/2006 | Gerdes et al. |
| 7,090,975 B2 | 8/2006 | Shultz et al. |
| 7,091,059 B2 | 8/2006 | Rhodes |
| 7,092,757 B2 | 8/2006 | Larson et al. |
| 7,097,973 B2 | 8/2006 | Zenhausern |
| 7,105,300 B2 | 9/2006 | Parce et al. |
| 7,106,089 B2 | 9/2006 | Nakano et al. |
| 7,129,554 B2 | 10/2006 | Lieber et al. |
| 7,169,560 B2 | 1/2007 | Lapidus et al. |
| 7,173,445 B2 | 2/2007 | Fujii et al. |
| 7,190,026 B2 | 3/2007 | Lotfi et al. |
| 7,192,745 B2 | 3/2007 | Jaeger |

(56) References Cited

U.S. PATENT DOCUMENTS

| | | |
|---|---|---|
| 7,193,453 B2 | 3/2007 | Wei et al. |
| 7,211,390 B2 | 5/2007 | Rothberg et al. |
| 7,220,550 B2 | 5/2007 | Keen |
| 7,223,540 B2 | 5/2007 | Pourmand et al. |
| 7,226,734 B2 | 6/2007 | Chee et al. |
| 7,229,799 B2 | 6/2007 | Williams et al. |
| 7,235,389 B2 | 6/2007 | Lim et al. |
| 7,238,323 B2 | 7/2007 | Knapp et al. |
| 7,239,188 B1 | 7/2007 | Xu et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,279,588 B2 | 10/2007 | Hong et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,526 B2 | 2/2008 | Peters et al. |
| 7,335,762 B2 | 2/2008 | Rothberg et al. |
| 7,359,058 B2 | 4/2008 | Kranz et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,462,709 B2 | 12/2008 | Jaeger |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,476,504 B2 | 1/2009 | Turner |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,534,097 B2 | 5/2009 | Wong et al. |
| 7,538,827 B2 | 5/2009 | Chou |
| 7,575,865 B2 | 8/2009 | Leamon et al. |
| 7,576,037 B2 | 8/2009 | Engelhardt et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee |
| 7,612,369 B2 | 11/2009 | Stasiak |
| 7,612,817 B2 | 11/2009 | Tay |
| 7,614,135 B2 | 11/2009 | Santini, Jr. et al. |
| 7,622,294 B2 | 11/2009 | Walt et al. |
| 7,645,596 B2 | 1/2010 | Williams et al. |
| 7,649,358 B2 | 1/2010 | Toumazou et al. |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,772,383 B2 | 8/2010 | Chakrabarti et al. |
| 7,785,785 B2 | 8/2010 | Pourmand et al. |
| 7,785,790 B1 | 8/2010 | Church et al. |
| 7,794,584 B2 | 9/2010 | Chodavarapu et al. |
| 7,821,806 B2 | 10/2010 | Horiuchi |
| 7,824,900 B2 | 11/2010 | Iwadate et al. |
| 7,838,226 B2 | 11/2010 | Kamahori et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,859,291 B2 | 12/2010 | Kim |
| 7,875,440 B2 | 1/2011 | Williams et al. |
| 7,884,398 B2 | 2/2011 | Levon et al. |
| 7,885,490 B2 | 2/2011 | Heideman et al. |
| 7,888,013 B2 | 2/2011 | Miyahara et al. |
| 7,888,015 B2 | 2/2011 | Toumazou et al. |
| 7,888,708 B2 | 2/2011 | Yazawa et al. |
| 7,890,891 B2 | 2/2011 | Stuber et al. |
| 7,898,277 B2 | 3/2011 | Weir |
| 7,923,240 B2 | 4/2011 | Su |
| 7,927,797 B2 | 4/2011 | Nobile et al. |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,972,828 B2 | 7/2011 | Ward et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,052,863 B2 | 11/2011 | Suzuki et al. |
| 8,067,731 B2 | 11/2011 | Matyjaszczyk et al. |
| 8,072,188 B2 | 12/2011 | Yorinobu et al. |
| 8,114,591 B2 | 2/2012 | Toumazou et al. |
| 8,124,936 B1 | 2/2012 | Lagna |
| 8,133,698 B2 | 3/2012 | Silver et al. |
| 8,138,496 B2 | 3/2012 | Li et al. |
| 8,154,480 B2 | 4/2012 | Shishido et al. |
| 8,199,859 B2 | 6/2012 | Zerbe et al. |
| 8,217,433 B1 | 7/2012 | Fife |
| 8,227,877 B2 | 7/2012 | Lee et al. |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,248,356 B2 | 8/2012 | Chen |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,277,628 B2 | 10/2012 | Ronaghi et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,357,547 B2 | 1/2013 | Lee et al. |
| 8,361,713 B2 | 1/2013 | Bridgham et al. |
| 8,383,396 B2 | 2/2013 | Kamahori et al. |
| 8,415,716 B2 | 4/2013 | Rothberg et al. |
| 8,421,437 B2 | 4/2013 | Levine |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,449,824 B2 | 5/2013 | Sun |
| 8,450,781 B2 | 5/2013 | Rothberg et al. |
| 8,470,164 B2 | 6/2013 | Rothberg et al. |
| 8,487,790 B2 | 7/2013 | Fife et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |
| 8,552,771 B1 | 10/2013 | Jordan et al. |
| 8,558,288 B2 | 10/2013 | Rothberg et al. |
| 8,575,664 B2 | 11/2013 | Rothberg et al. |
| 8,592,154 B2 | 11/2013 | Rearick et al. |
| 8,653,567 B2 | 2/2014 | Fife |
| 8,658,017 B2 | 2/2014 | Rothberg et al. |
| 8,673,627 B2 | 3/2014 | Nobile et al. |
| 8,685,230 B2 | 4/2014 | Rothberg et al. |

(56) References Cited

U.S. PATENT DOCUMENTS

| | | |
|---|---|---|
| 8,692,298 B2 | 4/2014 | Rothberg et al. |
| 8,728,844 B1 | 5/2014 | Liu et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,748,947 B2 | 6/2014 | Milgrew |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,776,573 B2 | 7/2014 | Rearick et al. |
| 8,786,331 B2 | 7/2014 | Jordan et al. |
| 8,796,036 B2 | 8/2014 | Fife et al. |
| 8,821,798 B2 | 9/2014 | Bustillo et al. |
| 8,823,380 B2 | 9/2014 | Levin et al. |
| 8,841,217 B1 | 9/2014 | Fife et al. |
| 8,847,637 B1 | 9/2014 | Guyton |
| 8,912,005 B1 | 12/2014 | Fife et al. |
| 8,945,912 B2 | 2/2015 | Bashir et al. |
| 8,962,366 B2 | 2/2015 | Putnam et al. |
| 8,963,216 B2 | 2/2015 | Fife et al. |
| 8,983,783 B2 | 3/2015 | Johnson et al. |
| 9,023,674 B2 | 5/2015 | Shen et al. |
| 9,164,070 B2 | 10/2015 | Fife |
| 9,201,041 B2 | 12/2015 | Dalton et al. |
| 9,270,264 B2 | 2/2016 | Jordan et al. |
| 9,389,199 B2 | 7/2016 | Cheng et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0012937 A1 | 1/2002 | Tender et al. |
| 2002/0029971 A1 | 3/2002 | Kovacs |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0081714 A1 | 6/2002 | Jain et al. |
| 2002/0085136 A1 | 7/2002 | Moon et al. |
| 2002/0086318 A1 | 7/2002 | Manalis et al. |
| 2002/0094533 A1 | 7/2002 | Hess et al. |
| 2002/0117694 A1 | 8/2002 | Migliorato et al. |
| 2002/0131899 A1 | 9/2002 | Kovacs |
| 2002/0150909 A1 | 10/2002 | Stuelpnagel et al. |
| 2002/0168678 A1 | 11/2002 | Williams et al. |
| 2002/0172963 A1 | 11/2002 | Kelley et al. |
| 2003/0020334 A1 | 1/2003 | Nozu |
| 2003/0032052 A1 | 2/2003 | Hadd et al. |
| 2003/0044799 A1 | 3/2003 | Matson |
| 2003/0044833 A1 | 3/2003 | Benchikh et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee et al. |
| 2003/0141929 A1 | 7/2003 | Casper et al. |
| 2003/0148301 A1 | 8/2003 | Aono et al. |
| 2003/0148344 A1 | 8/2003 | Rothberg et al. |
| 2003/0152929 A1 | 8/2003 | Howard |
| 2003/0152994 A1 | 8/2003 | Woudenberg et al. |
| 2003/0155942 A1 | 8/2003 | Thewes et al. |
| 2003/0175990 A1 | 9/2003 | Hayenga et al. |
| 2003/0186262 A1 | 10/2003 | Cailloux |
| 2003/0211502 A1 | 11/2003 | Sauer et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0002470 A1 | 1/2004 | Keith et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0134798 A1 | 7/2004 | Toumazou et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0017190 A1 | 1/2005 | Eversmann et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0058990 A1 | 3/2005 | Guia et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0093645 A1 | 5/2005 | Watanabe et al. |
| 2005/0106587 A1 | 5/2005 | Klapproth |
| 2005/0142033 A1 | 6/2005 | Glezer et al. |
| 2005/0151181 A1 | 7/2005 | Beintner et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0206548 A1 | 9/2005 | Muramatsu et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1 | 12/2005 | Fouillet et al. |
| 2005/0285155 A1 | 12/2005 | Johnson et al. |
| 2006/0000772 A1 | 1/2006 | Sano et al. |
| 2006/0024711 A1 | 2/2006 | Lapidus et al. |
| 2006/0035400 A1 | 2/2006 | Wu et al. |
| 2006/0040297 A1 | 2/2006 | Leamon et al. |
| 2006/0057025 A1 | 3/2006 | Eversmann et al. |
| 2006/0057604 A1 | 3/2006 | Chen et al. |
| 2006/0073513 A1 | 4/2006 | Chee et al. |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0216812 A1 | 9/2006 | Okada et al. |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0269927 A1 | 11/2006 | Lieber |
| 2006/0289726 A1 | 12/2006 | Paulus et al. |
| 2007/0059741 A1 | 3/2007 | Kamahori et al. |
| 2007/0069291 A1 | 3/2007 | Stuber et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0099208 A1 | 5/2007 | Drmanac et al. |
| 2007/0117099 A1 | 5/2007 | Engelhardt et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |

(56) References Cited

U.S. PATENT DOCUMENTS

| | | |
|---|---|---|
| 2007/0247170 A1 | 10/2007 | Barbaro et al. |
| 2007/0250274 A1 | 10/2007 | Volkov et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0035494 A1 | 2/2008 | Gomez et al. |
| 2008/0047836 A1 | 2/2008 | Strand et al. |
| 2008/0063566 A1 | 3/2008 | Matsumoto et al. |
| 2008/0077607 A1 | 3/2008 | Gatawood et al. |
| 2008/0085219 A1 | 4/2008 | Beebe et al. |
| 2008/0094074 A1 | 4/2008 | Kim et al. |
| 2008/0096216 A1 | 4/2008 | Quake et al. |
| 2008/0111161 A1 | 5/2008 | Sorge et al. |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0136933 A1 | 6/2008 | Dosluoglu et al. |
| 2008/0164917 A1 | 7/2008 | Floyd et al. |
| 2008/0176271 A1 | 7/2008 | Silver et al. |
| 2008/0178692 A1 | 7/2008 | Jung et al. |
| 2008/0185616 A1 | 8/2008 | Johnson et al. |
| 2008/0197022 A1 | 8/2008 | Suzuki et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |
| 2008/0286762 A1 | 11/2008 | Miyahara et al. |
| 2009/0026082 A1 | 1/2009 | Rothberg et al. |
| 2009/0030117 A1 | 1/2009 | Lanphere et al. |
| 2009/0033370 A1 | 2/2009 | Sarig et al. |
| 2009/0048124 A1 | 2/2009 | Leamon et al. |
| 2009/0062132 A1 | 3/2009 | Bortner |
| 2009/0075383 A1 | 3/2009 | El Gamal et al. |
| 2009/0079414 A1* | 3/2009 | Levon et al. ................ 324/71.5 |
| 2009/0120905 A1 | 5/2009 | Kohl et al. |
| 2009/0121258 A1 | 5/2009 | Kumar |
| 2009/0127589 A1 | 5/2009 | Rothberg et al. |
| 2009/0127689 A1 | 5/2009 | Ye et al. |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0201032 A1 | 8/2009 | Burdett et al. |
| 2009/0273386 A1 | 11/2009 | Korobeynikov et al. |
| 2010/0007326 A1 | 1/2010 | Nakazato |
| 2010/0026814 A1 | 2/2010 | Shimoda |
| 2010/0039146 A1 | 2/2010 | Park et al. |
| 2010/0052765 A1 | 3/2010 | Makino |
| 2010/0133547 A1 | 6/2010 | Kunze et al. |
| 2010/0137143 A1 | 6/2010 | Rothberg et al. |
| 2010/0176463 A1 | 7/2010 | Koizumi et al. |
| 2010/0188073 A1 | 7/2010 | Rothberg et al. |
| 2010/0197507 A1 | 8/2010 | Rothberg et al. |
| 2010/0244106 A1 | 9/2010 | Parker et al. |
| 2010/0273166 A1 | 10/2010 | Garcia |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0248320 A1 | 10/2011 | Rothberg et al. |
| 2011/0262903 A1 | 10/2011 | Rothberg et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife et al. |
| 2012/0001056 A1 | 1/2012 | Fife et al. |
| 2012/0001236 A1 | 1/2012 | Fife et al. |
| 2012/0001237 A1 | 1/2012 | Fife et al. |
| 2012/0001646 A1 | 1/2012 | Bolander et al. |
| 2012/0001779 A1 | 1/2012 | Fife et al. |
| 2012/0012900 A1 | 1/2012 | Lee et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife et al. |
| 2012/0060587 A1 | 3/2012 | Babcock et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0173159 A1 | 7/2012 | Davey et al. |
| 2012/0228136 A1 | 9/2012 | Levine |
| 2012/0247977 A1 | 10/2012 | Rothberg et al. |
| 2012/0249192 A1 | 10/2012 | Matsushita et al. |
| 2012/0261274 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |
| 2013/0056353 A1 | 3/2013 | Nemirovsky et al. |
| 2013/0105868 A1 | 5/2013 | Kalnitsky et al. |
| 2013/0135018 A1 | 5/2013 | Kuo et al. |
| 2013/0210128 A1 | 8/2013 | Rothberg et al. |
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0281307 A1 | 10/2013 | Li et al. |
| 2013/0324421 A1 | 12/2013 | Rothberg et al. |
| 2013/0341734 A1 | 12/2013 | Merz |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235452 A1 | 8/2014 | Rothberg et al. |
| 2014/0235463 A1 | 8/2014 | Rothberg et al. |
| 2014/0308752 A1 | 10/2014 | Chang et al. |

(56) References Cited

U.S. PATENT DOCUMENTS

| | | |
|---|---|---|
| 2015/0097214 A1 | 4/2015 | Chen et al. |
| 2016/0178568 A1 | 6/2016 | Cheng et al. |

FOREIGN PATENT DOCUMENTS

| | | |
|---|---|---|
| CN | 1703623 | 11/2005 |
| CN | 1826525 | 8/2006 |
| CN | 101676714 | 3/2010 |
| CN | 102203282 | 9/2011 |
| CN | 102301228 | 12/2011 |
| CN | 102484267 | 5/2012 |
| DE | 4232532 | 4/1994 |
| DE | 4430811 | 9/1995 |
| DE | 19512117 | 10/1996 |
| DE | 102004044299 | 3/2006 |
| DE | 102008012899 | 9/2009 |
| EP | 1975246 | 3/1984 |
| EP | 1243925 A2 | 9/2002 |
| EP | 1243925 A3 | 3/2003 |
| EP | 1557884 | 7/2005 |
| EP | 1669749 | 6/2006 |
| EP | 1870703 | 12/2007 |
| JP | 5870155 | 4/1983 |
| JP | 62-237349 | 10/1987 |
| JP | 02-250331 | 10/1990 |
| JP | 02-310931 | 12/1990 |
| JP | H05-080115 | 4/1993 |
| JP | H10-078827 | 3/1998 |
| JP | 2000055874 | 2/2000 |
| JP | 2002-221510 | 8/2002 |
| JP | 2002/272463 | 9/2002 |
| JP | PCT/JP2003/04697 | 4/2003 |
| JP | 2003-279532 | 10/2003 |
| JP | 2003-322633 | 11/2003 |
| JP | 2004-510125 | 4/2004 |
| JP | 2004-271384 | 9/2004 |
| JP | 2004-343441 | 12/2004 |
| JP | 2005077210 | 3/2005 |
| JP | 2005-515475 | 5/2005 |
| JP | 2005-207797 | 8/2005 |
| JP | 2006138846 | 6/2006 |
| JP | 2006-284225 | 10/2006 |
| JP | 2007/243003 | 9/2007 |
| JP | 2008-215974 | 9/2008 |
| JP | 2010513869 | 4/2010 |
| JP | 2012-506557 | 3/2012 |
| KR | 100442838 | 7/2004 |
| KR | 100455283 | 10/2004 |
| KR | 100455283 | 11/2004 |
| TW | 200510714 | 3/2005 |
| TW | 200946904 | 11/2009 |
| WO | WO-1990/005910 | 5/1990 |
| WO | 01/20039 | 3/2001 |
| WO | 01/42498 | 6/2001 |
| WO | 01/47804 | 7/2001 |
| WO | WO0181896 | 11/2001 |
| WO | 02/077287 | 10/2002 |
| WO | 02/086162 | 10/2002 |
| WO | 2004017068 | 2/2004 |
| WO | WO2004048962 | 6/2004 |
| WO | WO-2004081234 | 9/2004 |
| WO | WO2005015156 | 2/2005 |
| WO | 2005/022142 | 3/2005 |
| WO | WO2005043160 | 5/2005 |
| WO | WO2005062049 | 7/2005 |
| WO | 2005/073706 | 8/2005 |
| WO | 2005090961 | 9/2005 |
| WO | WO2005/090961 | 9/2005 |
| WO | 2006/056226 | 6/2006 |
| WO | WO2007002204 | 1/2007 |
| WO | 2008076406 | 6/2008 |
| WO | WO-2009/014155 | 1/2009 |
| WO | WO2009041917 | 4/2009 |
| WO | WO2009074926 | 6/2009 |
| WO | WO2009081890 | 7/2009 |
| WO | 2010/138186 | 12/2010 |
| WO | 2010/138188 | 12/2010 |
| WO | WO2012152308 | 11/2012 |
| WO | 2012/046137 | 12/2012 |

OTHER PUBLICATIONS

Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.
EP09798251.6 EP Extended Search Report Aug. 27, 2013.
EP11801437.2 EP Extended Search Report Jul. 25, 2013.
EP11801437.2 EP Search Report Jul. 8, 2014.
EP11801439.8 EP Extended Search Report Mar. 7, 2014.
EP11804218.3 EP Extended Search Report Jul. 11, 2013.
EP11827128.7 EP Search Report Aug. 1, 2013.
EP13161312.7 EP Extended Search Report Oct. 15, 2013.
EP13163995.7 EP Extended Search Report Aug. 20, 2013.
EP13163995.7 EP Search Report Jul. 9, 2014.
EP13164768.7 EP Extended Search Report Aug. 20, 2013.
EP13174555.6 EP Extended Search Report Dec. 12, 2013.
EP13174555.6 EP Search Report Nov. 21, 2013.
EP13177039.8 EP Search Report Nov. 21, 2013.
EP13177590.0 EP Search Report Nov. 20, 2013.
EP14152861.2 EP Search Report Jul. 7, 2014.
Eriksson, J. et al. "Pyrosequencing Technology at Elevated Temperature" Electrophoresis, vol. 25, 2004, pp. 20-27.
Hammond, et al., "Performance and System-On-Chip Integration of an Unmodified CMOS ISFET", Science Direct, Sensors and Actuators vol. 111-112, 2005, pp. 254-258.
Hizawa, et al. "Sensing Characteristics of Charge Transfer Type pH Sensor by Accumulative Operation" IEEE Sensors, EXCO, Daegu, Korea, 2006, pp. 144-147.
Ingebrandt, S. et al., "Label-free Detection of DNA using Field-Effect Transistors", Phys. stat. sol. (a) 203, No. 14, 2006, pp. 3399-3411.
Lee, S. et al. "An Enhanced Glucose Biosensor Using Charge Transfer Techniques" Biosensors and Bioelectronics, vol. 24, 2008, pp. 650-656.
Maki, W et al., "Nanowire-transistor based ultra-sensitive DNA methylation detection", Biosensors & Bioelectronics, vol. 23, 2008, pp. 780-787.
Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.
Nishiguchi, K. et al. "Si nanowire ion-sensitive field-effect transistors with a shared floating gate" Applied Physics Letters vol. 94, 2009 pp. 163106-1 to 163106-3.
Palan, B. et al., "New ISFET sensor interface circuit for biomedical applications", Sensors and Actuators B: Chemical: International Journal Devoted to Research and Development of Physical and Chemical Transducers, Elsevier S.A. Ch., vol. 57, No. 1-3, 1999, pp. 63-68.
PCT/US2011/042665 International Search Report and Written Opinion Nov. 2, 2011.
PCT/US2012/071471 International Preliminary Report on Patentability Jun. 24, 2014.
PCT/US2013/022129 International Preliminary Report on Patentability Jul. 22, 2014.
PCT/US2013/022129 International Search Report and Written Opinion Aug. 9, 2013.
PCT/US2013/022140 International Preliminary Report on Patentability Jul. 22, 2014.
PCT/US2014/020887 International Search Report and Written Opinion May 30, 2014.
PCT/US2014/020892 International Search Report and Written Opinion Jun. 3, 2014.
PCT/US2014/040923 International Search Report and Written Opinion Sep. 1, 2014.

(56) References Cited

OTHER PUBLICATIONS

Premanode, B. et al. "Drift Reduction in Ion-Sensitive FETs Using Correlated Double Sampling", Electronics Letters, IEEE Stevenage, GB, vol. 43 (16) Aug. 2, 2007.

Rothberg, J. et al., "An integrated semiconductor device enabling non-optical genome sequencing" Nature, vol. 475, No. 7356, 2011, pp. 348-352.

Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.

Tokuda, T. et al., "A CMOS image sensor with optical and potential dual imaging function for on-chip bioscientific applications", Sensors and Actuators A, vol. 125, No. 2, 2006, 273-280.

Wood, et al. "Base composition-independent hybridization in tetramethylammonium chloride: a method for oligonucleotide screening of highly complex gene libraries" Proc. Nat. Acad. Sci., 1985, pp. 1585-1588.

Zhao, B. et al., "Floating-Gate Ion Sensitive Field-Effect Transistor for Chemical and Biological Sensing", MRS Proceedings, vol. 828, 2004, pp. 349-354.

Ahmadian, A. et al., "Single-nucleotide polymorphism analysis by prosequencing", *Anal. Biochem.* vol. 280, 2000, pp. 103-110.

Gardner, J.W. et al., "Enhancing electronic nose performance by sensor selection using a new integer-based genetic algorithm approach", *Science Direct, Sensors and Actuators B*, vol. 106, 2005, pp. 114-121.

Hijikata, M. et al., "Identification of a Single Nucleotide Polymorphism in the MXA Gene Promoter (T/T at nt-88) Correlated with the Response of Hepatitis C Patients to Interferon", *Intervirology*, vol. 43, 2000, pp. 124-127.

Li, et al., "Sequence-Specific Label-Free DNA Sensors Based on Silico Nanowires", *Nano Letters*,, vol. 4(2), 2004, pp. 245-247.

Lin, B.J. et al., "Practicing the Novolac deep-UV portable conformable masking technique", *Journal of Vacuum Science and Technology*, Vo. 19, No. 4, 1981, 1313-1319.

Naidu, M. S. et al., "Introduction to Electrical Engineering", *Chapter 1—Fundamental Concepts of Electricity, McGraw Hill Education (India) Private Limited*, 1995, pp. 1-10.

Neaman, Donald A. , "Electronic Circuit Analysis and Design", *McGraw Hill Higher Education, 2nd edition, Chapter 6—Basic FET Amplifiers*, (reference will be uploaded in 2 parts due to size) part 1 of 2, Dec. 1, 2000, pp. 313-345.

Neaman, Donald A. , "Electronic Circuit Analysis and Design", *McGraw Hill Higher Education, 2nd edition, Chapter 6—Basic FET Amplifiers*, (reference will be uploaded in 2 parts due to size) part 2 of 2, Dec. 1, 2000, pp. 346-381.

PCT/JP2005/001987, "International Search Report", mailed Apr. 5, 2005.

PCT/JP2005/015522, "International Search Report", (includes English translation), mailed Sep. 27, 2005.

PCT/US2007/025721, "Declaration of Non-Establishment of International Search Report", mailed Jul. 15, 2008.

PCT/US2007/025721, "Written Opinion", mailed Jun. 16, 2009.

PCT/US2010/001553, "International Preliminary Report on Patentability", mailed Dec. 8, 2011, pp. 1-10.

PCT/US2010/001553, "International Search Report", mailed Jul. 28, 2010, pp. 1-2.

PCT/US2010/001553, "Written Opinion", mailed Jul. 14, 2010, pp. 1-6.

PCT/US2012/071482, "International Preliminary Amendment", mailed Jun. 24, 2014, 7 pages.

Ronaghi, M. et al., "A Sequencing Method Based on Real-Time Pyrophosphate", *Science*, vol. 281, 1998, 363-365.

Van Der Schoot, Bart et al., "The Use of a Multi-ISFET Sensor Fabricated in a Single Substrate", *Letter to the Editors, Sensors and Actuators*, vol. 12, 1987, pp. 463-468.

Vardalas, John , "Twists and Turns in the Development of the Transistor", *IEEE-USA Today's Engineer Online*, May 2003, 6 pages.

Wilhelm, D. et al., "pH Sensor Based on Differential Measurements on One pH-FET Chip", *Sensors and Actuators B*, vol. 4, 1991, pp. 145-149.

European Extended Search Report for European Application No. EP09822323.3 mailed May 27, 2015, 8 pages, PCT/US2009005745.

European Search Report for European Application No. EP10780930 mailed Jun. 15, 2015, 3 pages.

European Search Report for European Application No. EP10857377 mailed Jun. 26, 2015, 3 pages.

International Search Report and Written Opinion for International Application No. PCT/US2014/020892 mailed Jun. 3, 2014.

Temes, G.C. et al., "A Tutorial Discussion of the Oversampling Method for A/D and D/A Conversion", *1990 IEEE International Symposium on Circuits and Systems*, vol. 2 of 4, 1990, 5 pages.

Thewes, R. et al., "CMOS-based Biosencor Arrays", *Proceedings of the Design, Automation and Test in Europe Conference and Exhibition*, 2005, 2 pages.

Van Kerkhof, , "The Development of an ISFET based heparin sensor using the ion-step measuring method", *Biosensors and Bioelectronics*, vol. 9, Nos. 9-10, 1993, 463-472.

Yoshida, Shoji et al., "Development of a Wide Range pH Sensor based on Electrolyte-Insulator-Semiconductor Structure with Corrosion-Resistant $Al_2O_3$—$Ta_2O_5$ and $Al_2O_3$—$ZrO_2$", *Journal of the Electrochemical Society* vol. 151(3), 2004, pp. H53-H58.

Chin, Yuan-Lung et al., "Titanium Nitride Membrane Application to Extended Gate Field Effect Transistor pH Sensor Using VLSI Technology", *Jpn. J. Appl. Phys.* vol. 40, Part 1, No. 11, Nov. 2001, pp. 6311-6315.

International Preliminary Report on Patentability for International Application No. PCT/US2014/020887 mailed Sep. 15, 2015, 8 pages.

OV5640 Datasheet Product Specification, ¼" *color CMOS QSXGA (5 megapixel) image sensor with OmniBSI technology*, May 1, 2011, p. 1, line 9 and pp. 2-7, paragraph 1.

European Search Report for European Application No. EP10780935 dated Jun. 9, 2015, 5 pages.

Supplementary European Search Report for European Application No. EP10780935 dated Sep. 30, 2015, 6 pages.

European Search Report for European Application No. EP15170247.9 dated Nov. 10, 2015, 4 pages.

Ligler, Frances S. et al., "Array biosensor for detection of toxins", *Anal. Bioanal Chem* vol. 377, 2003, pp. 469-477.

Liu, Yan et al., "An ISFET based sensing array with sensor offset compensation and pH sensitivity enhancement", *Proc. of 2010 IEEE Int. Symp. on Circuits and Systems (ISCAS)*, ISBN:978-1-4244-5308-5, Jun. 2, 2010, pp. 2283-2286.

Matula, Richard A., "Electrical Resistivity of Copper, Gold, Palladium, and Silver", *Journal of Physical and Chemical Reference Data*, vol. 8.4, 1979, pp. 1147-1298.

Morgenshtein, Arkadiy et al., "Wheatstone-Bridge readout interface for ISFET/REFET applications", *Sensors and Actuators B: Chemical*, vol. 98, No. 1, Mar. 2004, pp. 18-27.

Nakazato, Kazuo, "An Integrated ISFET Sensor Array", *Sensors*, vol. 9, No. 11, 2009, 8831-8851.

Nakazato, Kazuro et al., "28p-Y-7 ISFET sensor array integrated circuits based on standard CMOS process", *The 55th annual meeting of the Japan Society of Applied Physics, book of Abstracts*, ISBN:978-4-903968-44-5, Mar. 27, 2008, p. 70.

Nakazato, Kazuro, "An Integrated ISFET Sensor Array", *Sensors*, Nov. 2009, vol. 9, No. 11, ISSN: 1424-8220, [online], Internet, URL, http://www.mdpi.com/1424-8220/9/11/8831/pdf, Nov. 2009, pp. 8831-8851.

International Preliminary Report on Patentability for International Application No. PCT/US2014/040923 dated Dec. 15, 2015, 8 pages.

International Search Report and Written Opinion of the International Searching Authority for International Application No. PCT/US2015/066052 dated Apr. 7, 2016, 19 pages.

Rowe, Chris A. et al., "An Array Immunosensor for Simultaneous Detection of Clinical Analytes", *Anal. Chem.* vol. 71, 1999, pp. 433-439.

(56) References Cited

OTHER PUBLICATIONS

Wen-Yaw, Chung A. et al., "New ISFET interface circuit design with tempreature Compensation", *CiteSeerx*—URL: http://citeseerx.ist.psu.edu/viewdoc/download?doi=10.1.1.95.2321&rep=rep1&type=pdf, 2006, 1.
Schroder, Dieter K., "6. Oxide and Interface Trapped Charges, Oxide Thickness", *Semiconductor Material and Device Characterization*, John Wiley & Sons, ISBN: 978-0-471-73906-7, Feb. 17, 2006, pp. 319-387.
PCT/US2015/066052, International Preliminary Reporrt on Patentability, dated Jun. 29, 2017, 1-16.
Eastman Kodak Company, "Image Sensor Solutions-Full-Frame CCD Image Sensor Performance Specification", www.physics.csbsju.edu/370/photometry/manuals/kaf-1001e.pdf, Feb. 19, 2001.
EP17167536.6, European Search Report, dated Nov. 7, 2017, 1-13.
TW103129092, Taiwan Search Report, dated Jan. 25, 2018, 1 pg.
TW106101966, Taiwan Search Report, dated Jan. 2, 2018, 1 pg.
JP2017-030653, Office Action (English Translation), dated Feb. 15, 2018, 1-4.

\* cited by examiner

100 p+ 110

100 p-epi 120 p+ 110

100 n+ 130 p-epi 120 p+ 110

CHEMICALLY SENSITIVE SENSOR WITH LIGHTLY DOPED DRAINS

RELATED APPLICATIONS

This application is a divisional of U.S. patent application Ser. No. 13/173,793 filed Jun. 30, 2011, which claims the benefit of U.S. Provisional Patent Application Ser. No. 61/361,403 filed on Jul. 3, 2010, each of which is incorporated herein by reference in its entirety.

BACKGROUND

Electronic devices and components have found numerous applications in chemistry and biology (more generally, "life sciences"), especially for detection and measurement of various chemical and biological reactions and identification, detection and measurement of various compounds. One such electronic device is referred to as an ion-sensitive field effect transistor, often denoted in the relevant literature as an "ISFET" (or pHFET). ISFETs conventionally have been explored, primarily in the academic and research community, to facilitate measurement of the hydrogen ion concentration of a solution (commonly denoted as "pH").

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analytes"). A detailed theory of operation of an ISFET is given in "Thirty years of ISFETOLOGY: what happened in the past 30 years and what may happen in the next 30 years," P. Bergveld, Sens. Actuators, 88 (2003), pp. 1-20 ("Bergveld"), which publication is hereby incorporated herein by reference in its entirety.

Details of fabricating an ISFET using a conventional CMOS (Complementary Metal Oxide Semiconductor) process may be found in Rothberg, et al., U.S. Patent Publication No. 2010/0301398, Rothberg, et al., U.S. Patent Publication No. 2010/0282617, and Rothberg et al, U.S. Patent Publication 2009/0026082; these patent publications are collectively referred to as "Rothberg", and are all incorporated herein by reference in their entirety. In addition to CMOS, however, biCMOS (i.e., bipolar and CMOS) processing may also be used, such as a process that would include a PMOS FET array with bipolar structures on the periphery. Alternatively, other technologies may be employed wherein a sensing element can be made with a three-terminal devices in which a sensed ion leads to the development of a signal that controls one of the three terminals; such technologies may also include, for example, GaAs and carbon nanotube technologies.

Taking a CMOS example, a P-type ISFET fabrication is based on a P-type silicon substrate, in which an N-type well forming a transistor "body" is formed. Highly doped P-type (P+) regions S and D, constituting a source and a drain of the ISFET, are formed within the N-type well. A highly doped N-type (N+) region B may also be formed within the N-type well to provide a conductive body (or "bulk") connection to the N-type well. An oxide layer may be disposed above the source, drain and body connection regions, through which openings are made to provide electrical connections (via electrical conductors) to these regions. A polysilicon gate may be formed above the oxide layer at a location above a region of the N-type well, between the source and the drain. Because it is disposed between the polysilicon gate and the transistor body (i.e., the N-type well), the oxide layer often is referred to as the "gate oxide."

Like a MOSFET, the operation of an ISFET is based on the modulation of charge concentration (and thus channel conductance) caused by a MOS (Metal-Oxide-Semiconductor) capacitance. This capacitance is constituted by a polysilicon gate, a gate oxide and a region of the well (e.g., N-type well) between the source and the drain. When a negative voltage is applied across the gate and source regions, a channel is created at the interface of the region and the gate oxide by depleting this area of electrons. For an N-well, the channel would be a P-channel (and vice-versa). In the case of an N-well, the P-channel would extend between the source and the drain, and electric current is conducted through the P-channel when the gate-source potential is negative enough to attract holes from the source into the channel. The gate-source potential at which the channel begins to conduct current is referred to as the transistor's threshold voltage VTH (the transistor conducts when VGS has an absolute value greater than the threshold voltage VTH). The source is so named because it is the source of the charge carriers (holes for a P-channel) that flow through the channel; similarly, the drain is where the charge carriers leave the channel.

As described in Rothberg, an ISFET may be fabricated with a floating gate structure, formed by coupling a polysilicon gate to multiple metal layers disposed within one or more additional oxide layers disposed above the gate oxide. The floating gate structure is so named because it is electrically isolated from other conductors associated with the ISFET; namely, it is sandwiched between the gate oxide and a passivation layer that is disposed over a metal layer (e.g., top metal layer) of the floating gage.

As further described in Rothberg, the ISFET passivation layer constitutes an ion-sensitive membrane that gives rise to the ion-sensitivity of the device. The presence of analytes such as ions in an analyte solution (i.e., a solution containing analytes (including ions) of interest or being tested for the presence of analytes of interest), in contact with the passivation layer, particularly in a sensitive area that may lie above the floating gate structure, alters the electrical characteristics of the ISFET so as to modulate a current flowing through the channel between the source and the drain of the ISFET. The passivation layer may comprise any one of a variety of different materials to facilitate sensitivity to particular ions; for example, passivation layers comprising silicon nitride or silicon oxynitride, as well as metal oxides such as silicon, aluminum or tantalum oxides, generally provide sensitivity to hydrogen ion concentration (pH) in an analyte solution, whereas passivation layers comprising polyvinyl chloride containing valinomycin provide sensitivity to potassium ion concentration in an analyte solution. Materials suitable for passivation layers and sensitive to other ions such as sodium, silver, iron, bromine, iodine, calcium, and nitrate, for example, are known, and passivation layers may comprise various materials (e.g., metal oxides, metal nitrides, metal oxynitrides). Regarding the chemical reactions at the analyte solution/passivation layer interface, the surface of a given material employed for the passivation layer of the ISFET may include chemical groups that may donate protons to or accept protons from the analyte solution, leaving at any given time negatively charged, positively charged, and neutral sites on the surface of the passivation layer at the interface with the analyte solution.

With respect to ion sensitivity, an electric potential difference, commonly referred to as a "surface potential," arises at the solid/liquid interface of the passivation layer and the analyte solution as a function of the ion concentration in the sensitive area due to a chemical reaction (e.g., usually involving the dissociation of oxide surface groups by the ions in the analyte solution in proximity to the sensitive area). This surface potential in turn affects the threshold voltage of the ISFET; thus, it is the threshold voltage of the ISFET that varies with changes in ion concentration in the analyte solution in proximity to the sensitive area. As described in Rothberg, since the threshold voltage $V_{TH}$ of the ISFET is sensitive to ion concentration, the source voltage $V_S$ provides a signal that is directly related to the ion concentration in the analyte solution in proximity to the sensitive area of the ISFET.

Arrays of chemically-sensitive FETs ("chemFETs"), or more specifically ISFETs, may be used for monitoring reactions—including, for example, nucleic acid (e.g., DNA) sequencing reactions, based on monitoring analytes present, generated or used during a reaction. More generally, arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such chemFET arrays may be employed in methods that detect analytes and/or methods that monitor biological or chemical processes via changes in charge at the chemFET surface. Such use of ChemFET (or ISFET) arrays involves detection of analytes in solution and/or detection of change in charge bound to the chemFET surface (e.g. ISFET passivation layer).

Research concerning ISFET array fabrication is reported in the publications "A large transistor-based sensor array chip for direct extracellular imaging," M. J. Milgrew, M. O. Riehle, and D. R. S. Cumming, Sensors and Actuators, B: Chemical, 111-112, (2005), pp. 347-353, and "The development of scalable sensor arrays using standard CMOS technology," M. J. Milgrew, P. A. Hammond, and D. R. S. Cumming, Sensors and Actuators, B: Chemical, 103, (2004), pp. 37-42, which publications are incorporated herein by reference and collectively referred to hereafter as "Milgrew et al." Descriptions of fabricating and using ChemFET or ISFET arrays for chemical detection, including detection of ions in connection with DNA sequencing, are contained in Rothberg. More specifically, Rothberg describes using a chemFET array (in particular ISFETs) for sequencing a nucleic acid involving incorporating known nucleotides into a plurality of identical nucleic acids in a reaction chamber in contact with or capacitively coupled to chemFET, wherein the nucleic acids are bound to a single bead in the reaction chamber, and detecting a signal at the chemFET, wherein detection of the signal indicates release of one or more hydrogen ions resulting from incorporation of the known nucleotide triphosphate into the synthesized nucleic acid.

Ion-sensitive metal oxide field effect transistors (ISFET) are known. The chemical reactions sensed by these types of transistors result in electrical signals that are very small in magnitude, and therefore may require amplification by additional circuitry to provide signal gain so the signal may be processed efficiently. The additional circuitry takes up real estate on the semiconductor substrate that may be used for additional sensor elements instead of amplification circuitry.

It would be beneficial if a chemically sensitive sensor could have a modified gain to eliminate the need for the additional gain circuitry. The inventor recognized the benefits of the following described embodiments.

DETAILED DESCRIPTION

Figures 1A, 1B, 1C, 1D:
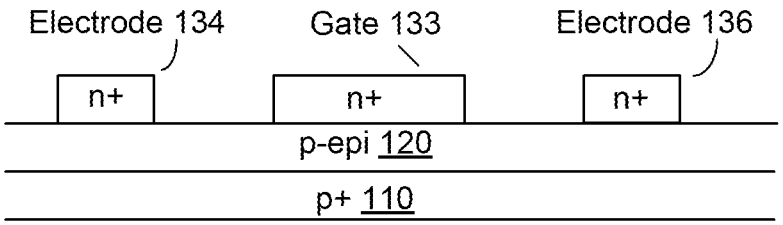
FIGS. 1A-D illustrate the building of a semiconductor substrate according to an embodiment of the present invention.

Embodiments provide a chemically sensitive sensor with modified gain. The chemically sensitive sensor may include a microwell, a floating gate terminal, a drain terminal, a source terminal and a pair of doped regions in a substrate. The microwell may accept a sample used in a chemical reaction. The floating gate may be electrically coupled to a gate electrode on the substrate. The drain terminal connection and the source terminal connection may be electrical terminals on the chemically sensitive sensor. The pair of doped regions in the substrate may each include a lightly doped region and a highly doped region. Each of lightly doped regions may extend beneath the gate electrode on the substrate and each of the highly doped regions may extend to couple respectively to the drain terminal and the source terminal.

Another embodiment may also provide a chemically sensitive sensor with modified gain. The chemically sensitive sensor may include a microwell, a floating gate terminal, a drain terminal, a source terminal, a pair of electrodes and a pair of doped regions in a substrate. The microwell may accept a sample used in a chemical reaction. The floating gate may be electrically coupled to a gate electrode on the substrate. The drain terminal connection and the source terminal connection may be electrical terminals on the chemically sensitive sensor. The pair of electrodes may be formed on the substrate and one electrode of the pair on either side of the gate electrode. One of the pair of doped regions may include a lightly doped region and a highly doped region, while the other one of the pair of doped regions may only include a highly doped region. The lightly doped region may extend beneath a respective one of the electrodes and the highly doped of each pair extends to couple respectively with the drain terminal or the source terminal.

An embodiment may also provide a method for building a chemically sensitive sensor according to an embodiment of the present invention. The method may forming a substrate with a first conductivity type of dopant. An epitaxial layer may be built using the same conductivity type dopant used to form the substrate, but made less dense than the dopant on the substrate. An electrode layer may be formed on the epitaxial layer formed from a different, second conductivity type of dopant than the first conductivity type of dopant used to form the substrate. The density of dopant on both the electrode layer and the substrate may be similar. The electrode layer may be masked and etched to produce gates and electrodes. A first lightly doped region may be created adjacent to one of the electrodes using a multidirectional implant technique, wherein the first lightly doped region is formed from a dopant of a conductivity type opposite the epitaxial layer dopant. Diffusion nodes may be produced that are self-aligned with the electrodes next to the gates, a first of said diffusion nodes contiguous with the first lightly doped region, from a dopant of a conductivity type similar to the gates, electrodes, and lightly doped region. A floating gate electrode, electrodes above the diffusion area, and contacts for electrodes may be formed by alternating layers of insulation, dielectric, conductive and metal layers.

FIGS. 1A-D illustrate the building of a semiconductor substrate according to an embodiment of the present invention. In this embodiment, the chemically sensitive sensor 100 may be fabricated on a polysilicon substrate 110 with a semiconductor doping, which in this example is a P or (P+)-type dopant, is formed as illustrated in FIG. 1A. As shown in FIG. 1B, an epitaxial layer (P-epi) 120 may be formed upon the P+ type substrate 110 from doping of similar conductivity type, i.e., P-type, as the P+ type substrate 110, but at a lesser density. Of course, other doping such as N-type doping may be used.

The area where the charge coupled sensor cells are going to be formed may be pre-doped at a dense doping level with a dopant having conductivity type opposite, i.e., N+, to that of the substrate (P+) 110 and epitaxial layer 120. In FIG. 1C, an N+ doping level 130 may be built over the P-type epitaxial layer 120 and the P+ type substrate 110. The N+ doping level 130 may be used within the charge coupled chemical sensor area. Using a mask and etching operation, gate(s) 133 and electrodes 134, 136 of the chemically sensitive sensor 100 may be formed in the pre-doped areas of the N+ doping levels 130 as shown in FIG. 1D. It will be understood by those of ordinary skill within the art that in the described embodiment, the doping levels can be reversed.

The above disclosed embodiment describes the fabrication of a transistor that may provide a first gain to any signal between the electrodes 134, 136 based on a signal applied to the gate electrode 133. The gain of the chemically sensitive sensor 100 may be modified by inserting additional doping material at locations within the substrate 110 in locations proximate to the electrodes 134, 136 or gate 133. The additional doping material may affect the capacitance of the transistor 100, which consequently modifies the gain of the transistor 100. The details of the gain modification will be explained in more detail with respect to FIG. 3.

Figure 2A:
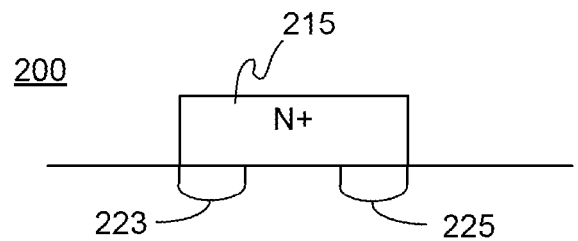
FIG. 2A-D illustrate a semiconductor doped to provide lightly doped drains according to an embodiment of the present invention.
Figure 2B:
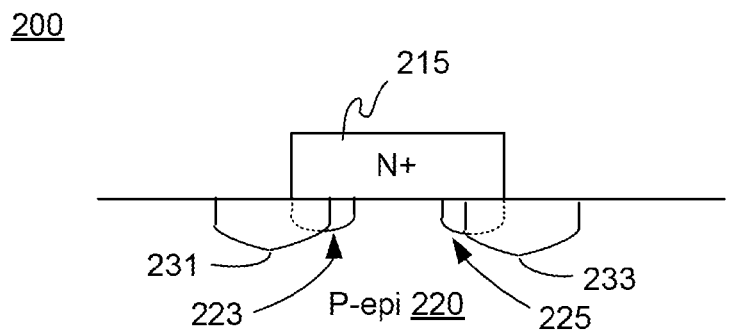

FIG. 2A illustrates an approximate location of additional doping in an epitaxial layer adjacent to a gate electrode according to an embodiment of the present invention. The device of FIG. 2A may have a substrate structure similar to that of FIG. 1C. The chemically sensitive sensor 200 may include an epitaxial layer 220 of a first conductivity type of dopant (i.e., P-type), a gate electrode 215 formed from a second conductivity type of dopant (i.e., N-type), and lightly doped regions 223, 225. The lightly doped regions 223, 225, also called lightly doped drains (LDD), may be of the same of conductivity type of dopant (i.e., P-type) as the gate electrode 215. The gain of the chemically sensitive sensor 200 may be modified by the injection of a less dense dopant in the lightly doped regions 223, 225 than the gate electrode 215. The lightly doped regions 223, 225 may be formed by using, for example, a multidirectional injection technique to inject the less-dense dopant into the lightly doped regions 223, 225 beneath the gate electrode 215. Of course, other techniques may also be used. Highly doped regions for the source and drain terminals of the transistor may be added either before or after the lightly doped regions. FIG. 2B illustrates the placement of diffusion nodes 223, 225, which may be highly doped regions, for coupling to the source and drain terminals of the chemically sensitive sensor 220 with respect to the gate electrode 215 and the lightly doped regions 223, 225. Using known doping techniques, the highly doped regions 223, 225 may be built with a high density dopant of the same conductivity type of dopant as the gate electrode 215.

Figure 2C:
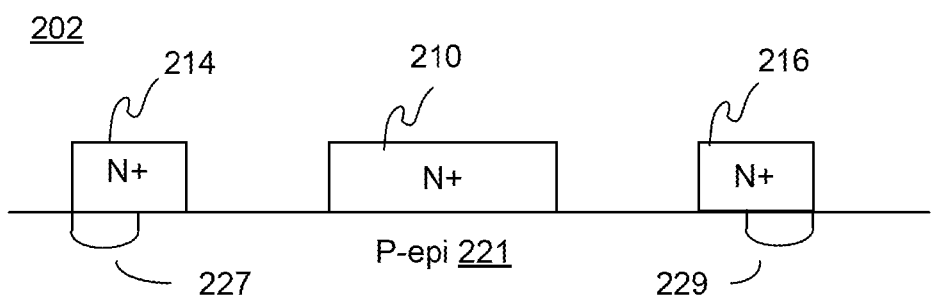
Figure 2D:
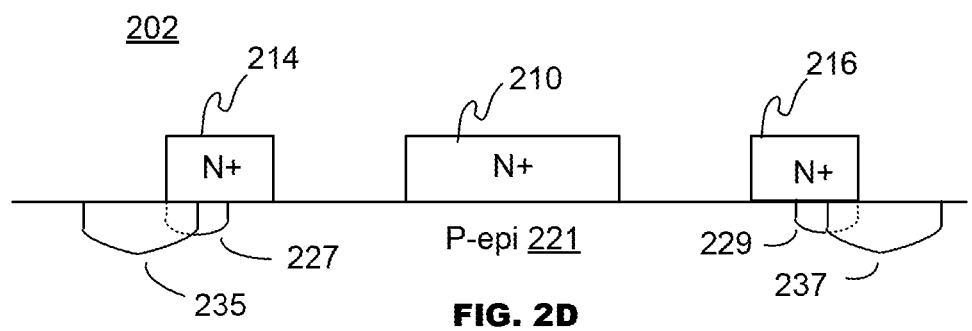

FIGS. 2C and 2D illustrate an alternative embodiment for a chemically sensitive sensor that has a modified doping. FIG. 2C illustrates a chemically sensitive sensor 202 that in addition to a gate 210 may also have electrodes 214, 216. In FIG. 2C, the gates 210 and the electrodes 214, 216 of the chemically sensitive sensor 202 can be masked to enable multidirectional doping implants to be inserted adjacent to respective electrodes 214, 216 to create lightly doped regions 227, 229, or lightly doped drains (LDD). The LDD 227 and 229 may be formed from a conductivity type opposite the epitaxial layer, i.e., N+. In the illustrated embodiment, the LDD 227, 229 may be formed within the chemically sensitive sensor 202 beneath the electrodes 214, 216. Alternatively, the LDD 227, 229 may be implanted using alternate implanting methods as are known in the art.

A photo resist layer can be used to mask desired areas and form diffusion nodes 235, 237 that may be self aligned with the electrodes 214, 216 next to the gates 210 and contiguous with the LDDs 227, 229. The diffusion areas 235 and 237 may be formed from a conductivity type similar to the gates 210, electrodes 214, 216 and LDDs 227, 229, and opposite from the conductivity type of the epitaxial layer 221. In FIG. 2D, the N+ diffusion nodes 237 and 239 may be highly doped regions and may be formed using any conventional technique known within the semiconductor arts. In addition, other nodes may also be formed. The lightly doped region 227, 229 may be doped at a dopant density level that is less than the dopant density level of the diffusion nodes 237 and 239.

Figure 3:
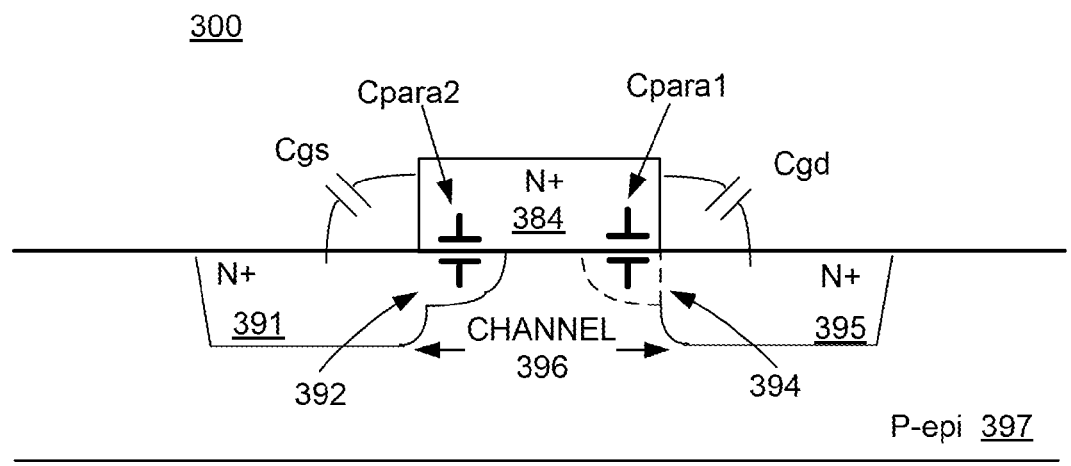
FIG. 3 illustrates a diagram of the capacitance generated by the respective doping regions of a chemically sensitive sensor in an embodiment of the present invention.

FIG. 3 is a diagram illustrating capacitances associated with the respective doping regions of a chemically sensitive sensor according to an embodiment of the present invention. The illustrated chemically sensitive sensor 300 may include a gate electrode 384 and diffusion areas 391 and 395 that are built on an epitaxial layer 397. The doping of the gate electrode 384 and diffusion areas 391, 395 is shown as N-type doping while the epitaxial layer 397 is shown as P-type. Of course, the doping may be reversed. The diffusion areas 391 and 395 may be doped at a high density. The diffusion area 391 may contact a source terminal of the chemically sensitive sensor 300 and the diffusion area 395 may contact a drain terminal of the chemically sensitive sensor 300. Of course, the source terminal and the drain terminal may be interchanged. The gate electrode 384 may connect to a floating gate (not shown) that will provide a signal. Depending upon the magnitude of the signal from the floating gate, the channel 396 may be induced to conduct according to known transistor principles. A signal on the drain diffusion area 395 may pass through the channel 396 to the source diffusion area 391. In addition, due to the fabrication of the sensor 300, a gate-to-drain capacitance Cgd may be present between the gate electrode 384 and the drain diffusion area 395. Similarly, a gate-to-source capacitance Cgs may be present between the gate electrode 384 and the source diffusion area 391. The values of these capacitances Cgd and Cgs may influence the signal gain of the sensor 300. The capacitance Cgd and Cgs may be the result of the junction area between the doping of the diffusion areas 391 and 395 and the gate electrode 384. A portion of the capacitance Cgd and Cgs may be attributed to parasitic capacitance at the junction of the diffusion area and the gate electrode 384. The amount of parasitic capacitance may be adjusted by adding lightly doped regions 394 and 392 to the drain and source diffusion areas 395 and 391, respectively. The lightly doped regions 394 and 392 may be doped at a lower density than the highly doped diffusion areas 391 and 395, but may add additional area at the junction of the diffusion areas 395 and 391 with the gate electrode 384. Due to the additional area, additional parasitic capacitance Cpara1 and/or Cpara2 may be present at the junction area. The density of the doping in the lightly doped areas will affect the amount of parasitic capacitance Cpara1 and/or Cpara2 created. Therefore, the total capacitance at the gate 384/drain diffusion area 395 may be approximately equal to Cgd+Cpara1, while the total capacitance at the gate 384/source diffusion area 391 may be approximately equal to Cgs+Cpara2.

The presence of parasitic capacitance values Cpara1 and/or Cpara2 may alter the gain of the sensor 300. In a pixel having an chemically-sensitive sensor (e.g., an ISFET) and a row selection transistor, the pixel may be read out in a source follower configuration or in a common source configuration. The parasitic capacitance values may affect the gain of the pixel in different ways depending on which configuration is used. In the source follower configuration, a gain of unity (1) is the maximum gain. Parasitic capacitors serve to attenuate the gain. This is because the signal at the fluidic interface is capacitively coupled to the floating gate of the chemically-sensitive sensor. The parasitic capacitors create a capacitive divider that reduces the charge to voltage conversion that occurs at the gate. Therefore, in source follower configurations, eliminating LDD regions and minimizing the parasitic capacitance provides the largest gain. In the common source configuration, it is desirable to control the parasitic capacitance in order to create negative feedback to establish systematic gain values. Without any parasitic capacitance, the pixel would operate open-loop during readout with a very large gain that is not well controlled by process parameters. Therefore, because LDD regions can be well controlled and consistently matched between devices, the gain can be controlled by these established capacitance values. In the common source configuration, the most important overlap capacitor is Cgd. The gain of the pixel is roughly equal to the double-layer capacitance divided by Cgd. By way of example, if the double layer capacitance is 3 fF and the value of Cgd is 0.3 fF, the gain of the pixel is approximately 10. This becomes a well controlled parameter when it is controlled by the LDD. To decrease the gain, Cgd is increased with larger LDD extensions. To increase the gain, the LDD extensions are reduced to lower Cgd. It is not desirable to have Cgd so small that it is not well controlled. Therefore, controlling the LDD region to achieve a gain in the range from 1 to 20 is desirable.

For example, in another embodiment, the lightly doped region 394 associated with the drain diffusion area 395 may be eliminated, and only the lightly doped region 392 may be present in a sensor 300. In this case, the capacitance attributed to the source terminal 391 may be equal to Cgs+Cpara2, while the capacitance attributed to the drain terminal 395 may only be equal to Cds. The gain of the sensor 300 in this embodiment is different from the embodiment described above in which both parasitic capacitances Cpara1 and Cpara2 were present. Accordingly, the addition of lightly doped regions 392 and/or 394 may be used to alter the gain of the sensor 300, and thereby eliminate additional circuitry that may be needed to amplify sensor 300 signal.

Figure 4:
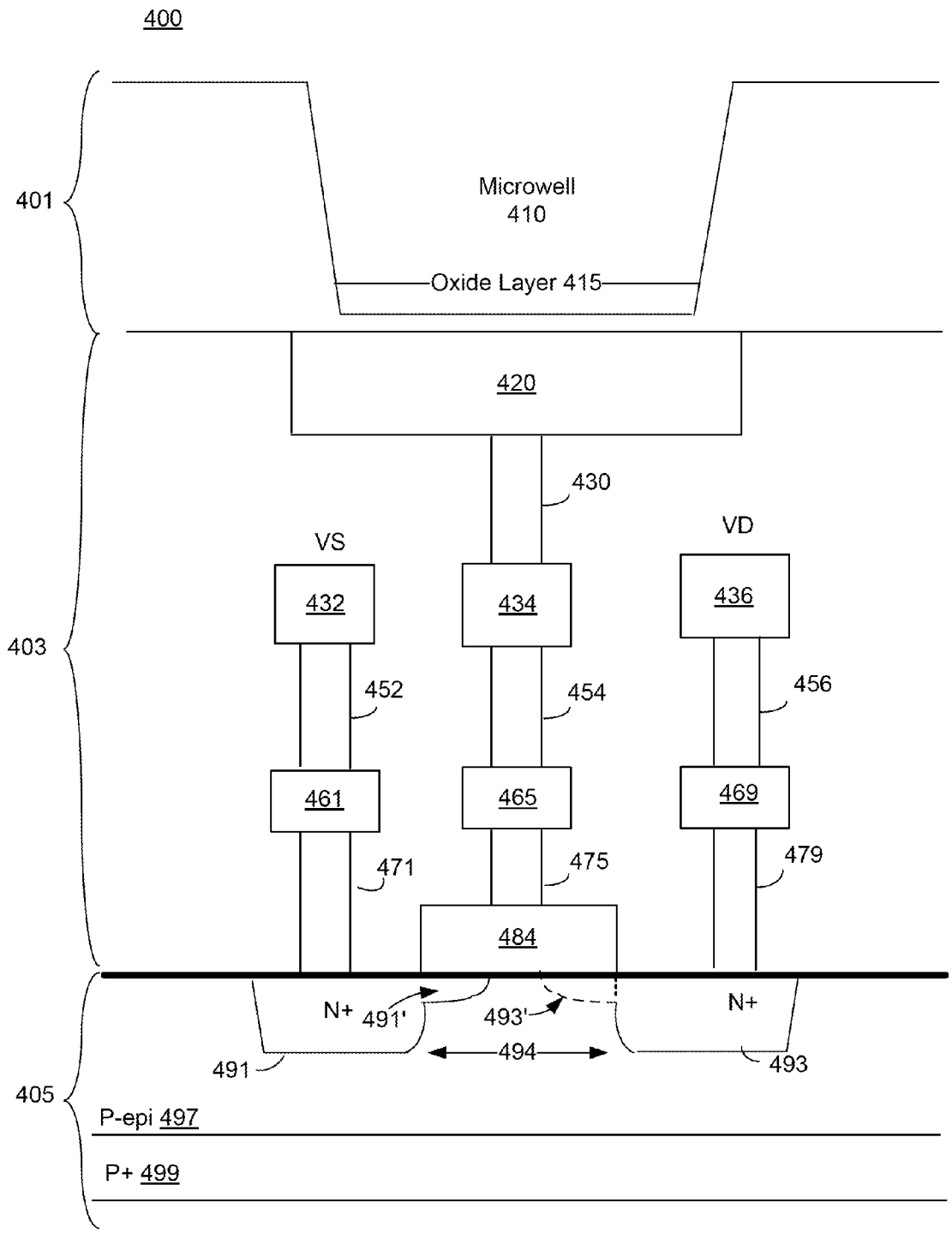
FIG. 4 illustrates an exemplary structure of a chemically sensitive sensor according to an embodiment of the present invention.

An exemplary illustration of a structure of a chemically sensitive sensor according to an embodiment of the present invention may be seen in FIG. 4. The chemically sensitive sensor 400 may include a microwell portion 401, a built-up portion 403, and a substrate portion 405. The microwell portion 401 may include a microwell 410 that may have a passivation layer, such as oxide layer 415, near the bottom of the microwell 410. A chemical reaction to be detected may occur in the microwell 410 and be detected by the a floating gate electrode 420 in the built-up portion 403.

The built-up portion 403 may include the floating gate electrode 420 built upon alternating layers of insulation and dielectric 432, 434, 436, 461, 465, 469; conductive and metal layers 430, 452, 454, 456, 471, 475 and 479; and a gate electrode 484. The substrate portion 405 may include a substrate 499 that may be doped with a P+ dopant, an epitaxial layer 497 that may also be a P-type dopant, and N+ doped regions 491 (source) and 493 (drain). The N+ doped regions 491 (source) and 493 (drain) may be highly doped regions, and the areas labeled 491' and 493' may be lightly doped regions. The channel 494 may become conductive based on the signal applied from floating gate 420 to the gate 484. Of course, the doping in the substrate 405, in the regions 491 and 493, in the epitaxial layer 497 and in gate 484 may be reversed.

The chemically sensitive sensor 400 may have, depending upon the mode of operation, a signal gain that is dependent, in part, upon the additional parasitic capacitance provided by the lightly doped regions 491' and/or 493' (if present). Embodiments of the chemically sensitive sensor 400 can either be an NMOS or PMOS device, e.g., formed as a standard NMOS or PMOS device with a microwell above a floating gate. The microwell structure 410 may contain an oxide or other material 415 that may transport a chemical sample, e.g., a specific ion(s), to sense a charge on the floating gate 420 of the chemically sensitive sensor 400. This charge transfer may then be read by read circuits (not shown) coupled to the chemically sensitive sensor 400 and the amount of charge transfer may represent an amount of ions contained within the sample in the microwell 410. It is in this way that each chemically sensitive sensor 400 in an array can be used to detect local variations in the sample in the microwell 410, for example, an ion concentration of a sample liquid, that is presented over an array (not shown) of chemically sensitive sensors 400.

Figure 5:
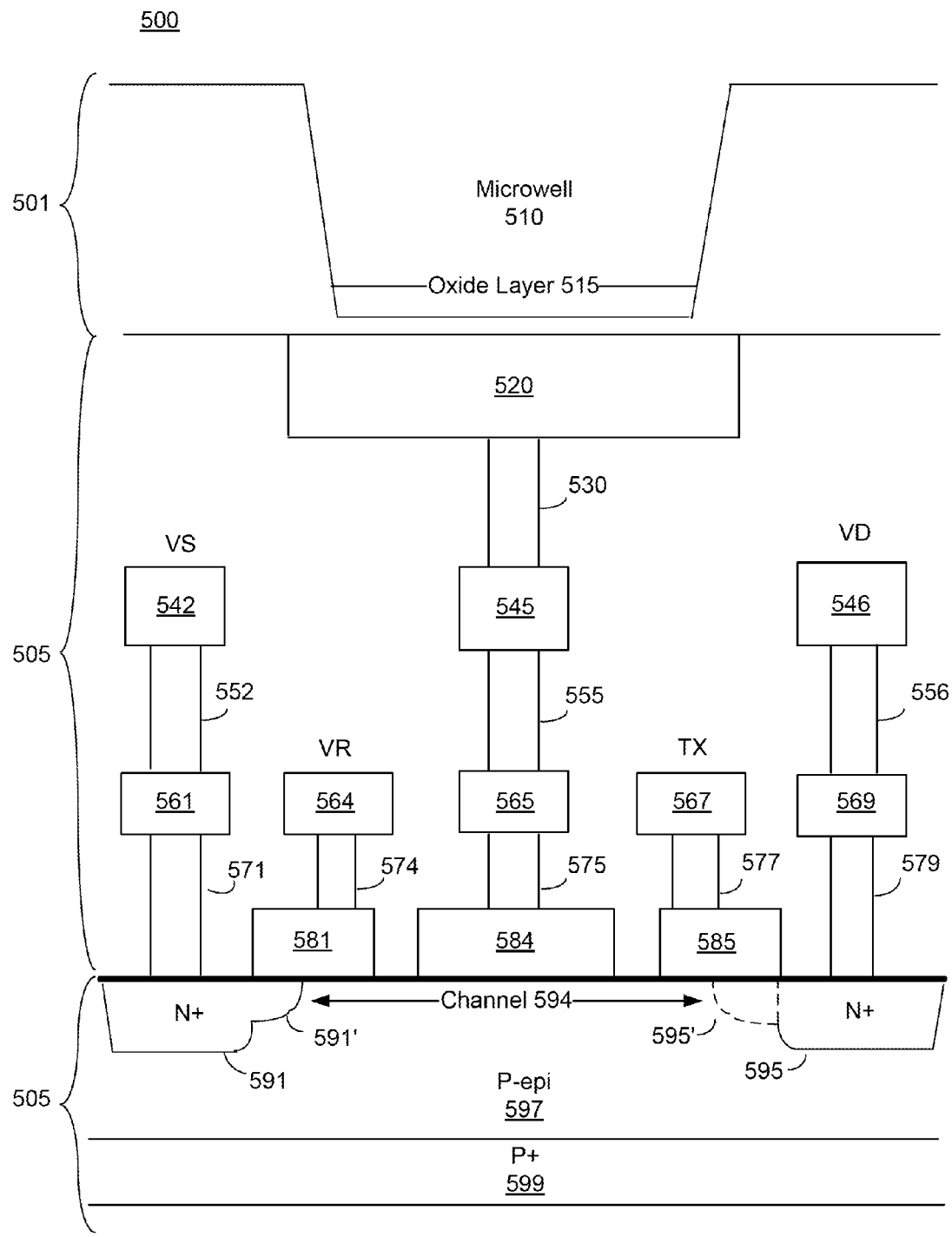
FIG. 5 illustrates another exemplary structure of a chemically sensitive sensor according to an embodiment of the present invention.

Another exemplary structure of a chemically sensitive sensor according to another embodiment of the present invention will be described with reference to FIG. 5. The chemically sensitive sensor 500 may include a microwell portion 501, a built-up portion 503, and a substrate portion 505. The microwell portion 501 may include a microwell 510 that may have a passivation layer, such as oxide layer 515, near the bottom of the microwell 510. The chemical reaction to be detected may occur in the microwell 510 and be detected by the a floating gate electrode 520 in the built-up portion 503.

The built-up portion 503 may include the floating gate electrode 520 built upon alternating layers of insulation and dielectric 542, 545, 546, 561, 565, 569 and conductive and metal layers 552, 555, 556, 571, 574, 575, 577 and 579. A gate electrode 584 and contacts 564, 567 can be formed for the electrodes 581 and 585. The substrate portion 505 may include a substrate 599 that may be doped with a P+ dopant, an epitaxial layer 597 that may also be a P-type dopant, and N+ doped regions 591 (source) and 595 (drain). Of course, the doping in the substrate 505 may be reversed. The electrodes 581 and 585 may accumulate charge from the gate electrode 584 to facilitate confinement and isolation. The charge coupling of the electrodes 581 and 585 with the gate electrode 584 may form a pixel that may be placed into an array for addressable readout. The transistor gain may be increased by the charge transfer from the gate electrode 584 to the electrodes 581 and 585. Furthermore, the charge transfer may be affected by the manipulation of the parasitic capacitance as explained above with respect to FIG. 3, which also affects the transistor gain. The parasitic capacitance may be manipulated by the addition of lightly doped regions 591' and/or 595', which may be doped at a lesser density than the highly doped regions 591 and 595. In addition, charge transfer may be also affected by the VR terminal 563 and the Tx terminal 585 that may act as barriers or wells for the charge packets.

It should be noted that embodiments using more or fewer metal and insulation layers are envisioned and the foregoing embodiments are simply exemplary examples. Additionally, the number of electrodes can vary greatly with differing embodiments. Following the formation of the floating gate electrode, any additional electrodes and contacts for the electrodes, the chemically sensitive sensors, including ions, can be formed by creating insulating or dielectric layers out of tetraethyl orthosilicate (TEOS) or oxides and etching microwells above the floating gate electrodes. The microwells can then have a passivation layer placed in at least the bottom of the microwell. Using the techniques described below, chemicals and ions can be sensed using structures made from processes similar to those described above. Varying embodiments of the foregoing structures are possible. For example, the gate electrodes may be formed using single layer polysilicon. The structure can be made using N+ or P+ electrodes. It is also envisioned that embodiments using single electrode polysilicon gap spacing makes it possible to charge couple the electrodes at a small enough process nodes such as 0.13 um and below. Process nodes 0.13 um and below enable a charge coupled structure to work in current CMOS processes. However, it should be noted that that process nodes are not limited to being this small, and can easily be larger. Embodiments employing surface channels, buried channels and using ion implantation to form channels stops using are also envisioned.

Additionally, embodiments using buried charge transfer with multiple N-type implants to create desired potential profiles to avoid interface states and avoid flicker noise are envisioned.

It should be noted that the previous description provides simply exemplary embodiments and that varying processes for the fabricating the chemical sensitive sensor disclosed herein will be readily apparent to those skilled in the art. For example, the lightly doped drains could be formed before the gates and electrodes using masking techniques. Accordingly, the steps discussed herein do not need to be performed in any particular order and may be performed using any semiconductor technique known within the art.

Several embodiments of the present invention are specifically illustrated and described herein. However, it will be appreciated that modifications and variations of the present invention are covered by the above teachings. In other instances, well-known operations, components and circuits have not been described in detail so as not to obscure the embodiments. It can be appreciated that the specific structural and functional details disclosed herein may be representative and do not necessarily limit the scope of the embodiments.

Those skilled in the art may appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disc Read Only Memory (CD-ROM), Compact Disc Recordable (CD-R), Compact Disc Rewriteable (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

What is claimed is:

1. A method of making a chemically sensitive sensor, comprising:
   forming a substrate with a first conductivity type of dopant;
   building an epitaxial layer using the same conductivity type dopant used to form the substrate, but made less dense than the dopant on the substrate;
   forming an electrode layer on the epitaxial layer formed from a different, second conductivity type of dopant than the first conductivity type of dopant used to form the substrate, wherein the density of dopant on both the electrode layer and the substrate are similar;
   masking and etching the electrode layer to produce gates and corresponding electrode pairs;
   creating a first lightly doped region adjacent to one electrode of each of the electrode pairs using a multi-directional implant technique, wherein the first lightly doped region is formed from a dopant of a conductivity type opposite the epitaxial layer dopant;
   producing diffusion nodes that are self-aligned with the electrode pairs, a first of said diffusion nodes contiguous with the first lightly doped region, from a dopant of a conductivity type similar to the gates, electrode pairs, and lightly doped region; and
   forming a floating gate electrode, and contacts for the electrode pairs by alternating layers of insulation, dielectric, conductive and metal layers.

2. The method of claim 1, further comprising:
   creating a second lightly doped region adjacent to the other electrode of each of the electrode pairs using a multidirectional implant technique, wherein the second lightly doped region is formed from a dopant of a conductivity type opposite the epitaxial layer dopant.

3. The method of claim 1, wherein a second of said diffusion nodes is contiguous with a second lightly doped region.

4. The method of claim 1, further comprising:
   forming an additional electrode on the diffusion nodes.

5. The method of claim 1, further comprising:
   forming a microwell to hold a sample above the floating gate.

* * * * *